US010258268B2

United States Patent
Roblyer et al.

(10) Patent No.: US 10,258,268 B2
(45) Date of Patent: Apr. 16, 2019

(54) HIGH-SPEED TISSUE OXIMETRY SYSTEM EMPLOYING FAST DIGITAL DIFFUSE OPTICAL SPECTROSCOPY

(71) Applicant: Trustees of Boston University, Boston, MA (US)

(72) Inventors: Darren Roblyer, Boston, MA (US); Alyssa Torjesen, Charlestown, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 15/960,747

(22) Filed: Apr. 24, 2018

(65) Prior Publication Data

US 2018/0303391 A1 Oct. 25, 2018

Related U.S. Application Data

(60) Provisional application No. 62/489,677, filed on Apr. 25, 2017.

(51) Int. Cl.
*A61B 5/1455* (2006.01)
*A61B 5/00* (2006.01)
*A61B 5/1495* (2006.01)

(52) U.S. Cl.
CPC ........ *A61B 5/14551* (2013.01); *A61B 5/1495* (2013.01); *A61B 5/7203* (2013.01); *A61B 5/742* (2013.01)

(58) Field of Classification Search
CPC . A61B 5/0205; A61B 5/02416; A61B 5/0059; A61B 5/14542; A61B 5/1455;
(Continued)

(56) References Cited

U.S. PATENT DOCUMENTS 5,497,769 A * 3/1996 Gratton .............. A61B 5/0059
356/41
6,195,574 B1 * 2/2001 Kumar .............. A61B 5/14553
600/310
(Continued)

FOREIGN PATENT DOCUMENTS

WO 20160164894 10/2016

OTHER PUBLICATIONS

Farzam, Parisa, et al., "Pulsatile and Steady-State Hemodynamics of the Human Patella Bone by Diffuse Optical Spectroscopy", Publication, IOP Science, Physiol. Meas. 34 (2013) 839-857, published Jul. 17, 2013.
(Continued)

*Primary Examiner* — Eric Winakur
*Assistant Examiner* — Chu Chuan (JJ) Liu
(74) *Attorney, Agent, or Firm* — BainwoodHuang

(57) ABSTRACT

A tissue oximetry system employing diffuse optical spectroscopy includes an optical subsystem and an electronics and processing subsystem, together generating modulated optical signals processing a response optical signal in order to obtain measurements of blood oxygen values for a tissue from per-wavelength absorption values. Signal sources generate RF modulation signals, and ADC circuitry generates streams of digital sample values from analog detection signals. Data acquisition circuitry and a processor (1) provide RF modulation command values in synchronism with sampling operation according to an offset pattern and rate, stepping through an RF range to obtain measurements of the absorption values in measurement intervals at least 10 times per second, (2) in each of the measurement intervals, calculate the model to obtain the blood oxygen values from the measurements of the absorption values, and display or
(Continued)

otherwise use the obtained blood oxygen values in higher-level diagnostic assessment of tissue blood oxygenation.

14 Claims, 9 Drawing Sheets

(58) Field of Classification Search
CPC ............ A61B 5/14551; A61B 5/14552; A61B 5/14553; A61B 5/7228
See application file for complete search history.

(56) References Cited

U.S. PATENT DOCUMENTS

| | | | |
|---|---|---|---|
| 6,216,021 B1* | 4/2001 | Franceschini | A61B 5/14551 600/310 |
| 8,386,000 B2* | 2/2013 | McKenna | A61B 5/14551 600/310 |
| 8,712,492 B2* | 4/2014 | Lisogurski | A61B 5/1455 600/310 |

OTHER PUBLICATIONS

Park, Kyoungsu, et al., "A Compact, Multi-Wavelength, and High Frequency Response Light Source for Diffuse Optical Spectroscopy and Imaging", Conference Publication, Proceedings of SPIE, SPIE BiOS, San Franscisco, CA, 2015.

Lee, Jangwoen, et al., "Broadband Diffuse Optical Spectroscopy Assessment of Hemorrhage- and Hemoglobin-Based Blood Substitute Resuscitation", Publication, Journal of Biomedical Optics, vol. 14(4), pp. 044027-1 to 044027-7, Jul./Aug. 2009.

Zhao, Yan, et al., "Portable, Parallel 9-Wavelength Near-Infrared Spectral Tomography (NIRST) System for Efficient Characterization of Breast Cancer Within the Clinical Oncology Infusion Suite", Publication, Biomedical Optics Express 2186, vol. 7, No. 6, May 16, 2016.

"National Cancer Institute: Surveillance, Epidemiology, and End Results Program." [Online]. Available: http://seer.cancer.gov/statfacts/html/breast.html. (Wayback Machine Archive), Mar. 2017.

Kuerer, B.H.M. et al., "Clinical Course of Breast Cancer Patients With Complete Pathologic Primary Tumor and Axillary Lymph Node Response to Doxorubicin-Based Neoadjuvant Chemotherapy", Publication, Journal of Clinical Oncology, vol. 17, No. 2, pp. 460-469, 1999.

Miller, MD, Marian, et al., "Tumor Response Ratio Predicts Overall Survival in Breast Cancer Patients Treated with Neoadjuvant Chemotherapy", Publication, Annals of Surgical Oncology, vol. 21, pp. 3317-3323, 2014.

Caudle, Abigail S., et al., "Predictors of Tumor Progression During Neoadjuvant Chemotherapy in Breast Cancer", Publication, Journal of Clinical Oncology, vol. 28, No. 11, pp. 1821-1828, 2010.

Rastogi, Priya, et al., "Preoperative Chemotherapy: Updates of National Surgical Adjuvant Breast and Bowel Project Protocols B-18 and B-27", Publication, Journal of Clinical Oncology, vol. 26, No. 5, pp. 778-785, 2008.

Silverstein, Melvin J., et al., "Special Report:Consensus Conference III. Image-Detected Breast Cancer: State-of-the-Art Diagnosis and Treatment", Publication, Journal of the American College of Surgeons, vol. 209, No. 4, pp. 504-520, 2009.

Zakhireh, Jennifer, et al., "Converting Evidence to Practice: A Guide For the Clinical Application of MRI For the Screening and Management of Breast Cancer", Publication, European Journal of Cancer, vol. 44, No. 18, pp. 2742-2752, 2008.

Soliman, Hany, et al., "Functional Imaging Using Diffuse Optical Spectroscopy of Neoadjuvant Chemotherapy Response in Women with Locally Advanced Breast Cancer", Publication, Clinical Cancer Research, vol. 16, No. 9, pp. 2605-2615, 2010.

Anderson, Pamela G., et al., "Broadband Optical Mammography: Chromophore Concentration and Hemoglobin Saturation Contrast in Breast Cancer," Publication, PLoS One, vol. 10, No. 3, pp. 1-23, 2015.

Cerussi, Albert, et al., "Predicting Response to Breast Cancer Neoadjuvant Chemotherapy Using Diffuse Optical Spectroscopy", Publication, Proceedings of the National Academy of Sciences of the United States of America, vol. 104, No. 10, pp. 4014-4019, Mar. 2007.

Roblyer, Darren, et al., "Optical Imaging of Breast Cancer Oxyhemoglobin Flare Correlates With Neoadjuvant Chemotherapy Response One Day After Starting Treatment", Publication, Proceedings of the National Academy of Sciences of the United States of America, vol. 108, No. 35, pp. 14626-14631, 2011.

Tromberg, Bruce J., et al., "Non-Invasive Measurements of Breast Tissue Optical Properties Using Frequency-Domain Photon Migration", Publication, Philosophical Transactions of the Royal Society of London. Series B, Biological Sciences, vol. 352, No. 1354, pp. 661-668, 1997.

Tromberg, Bruce J., et al., "Optical Property Measurements in Turbid Media Using Frequency Domain Photon Migration", Publication, Proceedings of SPIE, vol. 1525, pp. 52-58, 1991.

Cerussi, A., et al., "Diffuse Optical Spectroscopic Imaging (DOSI)" [Online]. Available: https://sites.google.com/site/dosiatbli/home. (Wayback Machine Archive), Jun. 2015.

Jacques, Steven L., "Optical Properties of Biological Tissues: A Review", Publication, Physics in Medicine and Biology, vol. 58, pp. R37-R61, 2013.

Fishkin, Joshua, et al., "Diffusion of Intensity Modulated Near-Infrared Light in Turbid Media", Publication, Proceedings of SPIE, vol. 1431, pp. 122-135, 1991.

Pham, Tuan H., et al., "Broad Bandwidth Frequency Domain Instrument for Quantitative Tissue Optical Spectroscopy", Publication, Review of Scientific Instruments, vol. 71, No. 6, pp. 83-100, 2000.

Haskell, Richard C., et al., "Boundary Conditions For the Diffusion Equation in Radiative Transfer", Publication, Journal of the Optical Society of America. A, Optics, Image Science, and Vision, vol. 11, No. 10, pp. 2727-2741, 1994.

Netz, Uwe J., et al., "Multipixel System for Gigahertz Frequency-Domain Optical Imaging of Finger Joints", Publication, Review of Scientific Instruments, vol. 79, pp. 1-14, 2008.

O'Sullivan, Thomas D., et al., "Diffuse Optical Imaging Using Spatially and Temporally Modulated Light", Publication, Journal of Biomedical Optics, vol. 17, No. 7, p. 071311, 2012.

Zijlstra, W.G., et al., "Spectrophotometry of Hemoglobin: Absorption Spectra of Bovine Oxyhemoglobin, Deoxyhemoglobin, Carboxyhemoglobin, and Methemoglobin", Publication, Comparative Biochemistry and Physiology, vol. 118, No. 4, pp. 743-749, 1997.

McBride, Troy O., et al., "A Parallel-Detection Frequency-Domain Near-Infrared Tomography System for Hemoglobin Imaging of the Breast in Vivo", Publication, Review of Scientific Instruments, vol. 72, No. 3, pp. 1817-1824, 2001.

Culver, J.P., et al., "Three-Dimensional Diffuse Optical Tomography in the Parallel Plane Transmission Geometry: Evaluation of a Hybrid Frequency Domain/Continuous Wave Clinical System for Breast Imaging", Publication, Medical Physics, vol. 30, No. 2, pp. 235-247, 2003.

Zimmermann, Bernhard B., et al.. "Frequency Domain Near-Infrared Multiwavelength Imager Design Using High-Speed, Direct Analog-to-Digital Conversion", Publication, Journal of Biomedical Optics, vol. 21, No. 1, p. 016010, 2016.

Yu, Guoqiang, et al., "Frequency-Domain Multiplexing System for in Vivo Diffuse Light Measurements of Rapid Cerebral Hemodynamics", Publication, Applied Optics, vol. 42, No. 16, pp. 2931-2939, 2003.

Weigel, Udo M., et al., "A New, Modular Frequency Domain Diffuse Optical Monitor in the Digital Domain", Publication, Biomedical Optics and 3D Imaging OSA, 2012.

Pogue, Brian W., et al., "Instrumentation and Design of a Frequency-Domain Diffuse Optical Tomography Imager for Breast Cancer Detection", Publication, Optics Express, vol. 1, No. 13, pp. 391-403, 1997.

(56) References Cited

OTHER PUBLICATIONS

Yang, Yunsong, et al., "Low-Cost Frequency-Domain Photon Migration Instrument for Tissue Spectroscopy, Oximetry, and Imaging", Publication, Optical Engineering, vol. 36, No. 5, pp. 1562-1569, 1997.
Madsen, Steen J., et al., "A High-Bandwidth Frequency-Domain Photon Migration Instrument for Clinical Use", Publication, Proceedings of SPIE, 1995, vol. 2389, pp. 257-263.
No, Keun-Sik, "Design and Testing of Miniature Broadband Frequency Domain Photon Migration Instrument", Publication, Journal of Biomedical Optics, vol. 13, No. 5, p. 050509, 2009.
Roblyer, Darren, et al., "Feasibility of Direct Digital Sampling for Diffuse Optical Frequency Domain Spectroscopy in Tissue", Publication, Measurement Science & Technology, vol. 24, No. 4, p. 045501, 2013.
Jung, Justin, et al., "Note: A Simple Broad Bandwidth Undersampling Frequency-Domain Digital Diffuse Optical Spectroscopy System", Publication, Review of Scientific Instruments, vol. 85, No. 7, pp. 72-75, 2014.
Bland, J. Martin, et al., "Statistical Methods for Assessing Agreement Between Two Methods of Clinical Measurement", Publication, International Journal of Nursing Studies, vol. 47, No. 8, pp. 931-936, 2010.
Shah, Natasha, et al., "Spatial Variations in Optical and Physiological Properties", Publication, Journal of Biomedical Optics, vol. 9, No. 3, pp. 534-540, 2004.
Foo, Jong Yong Abdiel, et al., "Pulse Transit Time Based on Piezoelectric Technique at the Radial Artery", Publication, Journal of Clinical Monitoring and Computing, vol. 20, pp. 185-192, 2006.

\* cited by examiner

Fig. 4

$$\frac{1}{c}\frac{\partial \phi(\mathbf{r},t)}{\partial t} - D\nabla^2 \phi(\mathbf{r},t) + \mu_a \phi(\mathbf{r},t) = S(\mathbf{r},t)$$

$$\Theta_{\text{lag}}(\rho,\omega) = k_{\text{imag}}(\omega)\rho,$$

$$A_{\text{att}}(\rho,\omega) = \frac{\exp[-k_{\text{real}}(\omega)\rho]}{4\pi D\rho}$$

$$k_{\text{real}} = \sqrt{\frac{3}{2}\mu_a\mu_s'}\left\{\left[1+\left(\frac{\omega}{c\mu_a}\right)^2\right]^{1/2}+1\right\}^{1/2},$$

$$k_{\text{imag}} = \sqrt{\frac{3}{2}\mu_a\mu_s'}\left\{\left[1+\left(\frac{\omega}{c\mu_a}\right)^2\right]^{1/2}-1\right\}^{1/2}$$

HIGH-SPEED TISSUE OXIMETRY SYSTEM EMPLOYING FAST DIGITAL DIFFUSE OPTICAL SPECTROSCOPY

STATEMENT OF GOVERNMENT RIGHTS

The invention was made with Government support under contract no. W81XWH-15-1-0070 awarded by the Department of the Army. The Government has certain rights in the invention.

BACKGROUND

The invention relates to the field of tissue oximetry systems used for measuring blood oxygenation of in vivo tissue.

The adequate delivery of oxygen to internal organs and tissue is a fundamental requirement for normal biological function, and inadequate delivery can be a sign of pulmonary, cardiac, or vascular complications, all of which require immediate intervention. Despite the importance of tissue oxygenation, the development of clinical technologies for monitoring this parameter has largely stagnated over the last 30 years, and current techniques are limited by their inability to measure key parameters in both the arterial and vascular components, and by the invasive nature of their implementation (e.g. invasive catheters), leading to false diagnoses, late interventions, and infection.

Pulse-oximetry and co-oximetry probes can be found in almost all doctor's offices, intensive care units, surgical suites, endoscopy suites, delivery suites and in most hospital settings. This technology is used to optically monitor arterial oxygen saturation using a simple finger, toe, or ear clip. Adequate tissue oxygenation is necessary for normal organ function and arterial oxygen saturation in a healthy individual is typically between 95-100%. Any decrease below these values (hypoxemia) is cause for immediate intervention, and may indicate inadequate blood oxygenation by the lungs, inadequate blood flow from the heart, or peripheral vasculature problems including shock.

Despite the ubiquity of pulse oximetry, the current technology is incapable of measuring potentially lifesaving information about the oxygen content in the arterial and venous circulation. For example, pulse oximetry cannot measure the quantity or concentration of blood in the peripheral vasculature, which is important for shock differential diagnosis. Pulse oximetry is also incapable of measuring venous oxygen saturation ($SvO_2$) or venous blood concentration, which provides important information related to tissue oxygen extraction, and which currently requires the use of an invasive fiber optic probe catheter in the pulmonary artery, a procedure that carries risk of mechanical damage to the heart and important blood vessels, and infection. New noninvasive and quantitative tissue oxygenation methods are needed to improve patient care at the bedside.

SUMMARY

Diffuse Optical Spectroscopy (DOS) has emerged as a noninvasive method to characterize optical scattering and absorption and, in turn, calculate concentrations of optically responsive substances (chromophores) in thick tissue. Of particular interest is measurement of concentrations of blood oxygenation values, i.e., oxyhemoglobin and deoxyhemoglobin. Diffuse optical methodologies can be broadly categorized into three distinct measurement types: time domain (TD), frequency domain (FD), and continuous wave (CW). A disclosed system employs FD-DOS, which allows for the separation of optical scattering and absorption through the measurement of amplitude attenuation and phase delay of photon density waves generated by intensity modulated light sources at the tissue surface.

Prior FD-DOS systems have employed network analyzers and thus have relatively large instrument footprints as well as high cost. Furthermore, FD-DOS instruments often have slow measurement acquisition speeds compared to CW counterparts, and data acquisition speeds have been limited for broad modulation frequency bandwidth FD-DOS systems.

Described herein is an FD-DOS system that fully integrates digital signal synthesis and detection to rapidly acquire multi-wavelength, multiplexed, broadband frequency sweep measurements at a high repetition rate, e.g., 10 Hz or greater. This high-speed, broad-bandwidth, digital, DOS system minimizes analog circuitry while reducing cost and device footprint, potentially enabling access to more patients in the clinic and expanding the capabilities of this technology, especially for monitoring fast physiological changes. In particular, the fast sampling ability can be used to obtain multiple blood oxygenation measurements throughout the cardiac cycle, providing a unique view of cardiac function beyond that provided by an ECG for example.

More particularly, a tissue oximetry system is disclosed that comprises an optical subsystem including a plurality of optical sources and one or optical detectors, the optical sources being configured and operative to generate a set of optical signals of distinct wavelengths modulated according to respective RF modulation signals applied thereto. The set of wavelengths and the RF modulation signals are selected according to a model for (1) obtaining absorption values and scattering values from per-wavelength amplitude and phase responses, and (2) obtaining measurements of blood oxygen values from the absorption and scattering values for the wavelengths. The optical signals collectively form an incident optical signal directed to a sample location of a tissue, and the optical detectors are configured and operative to generate one or more analog detection signals indicative of amplitude and phase of RF modulation components of a detected optical signal emanating from the sample location in response to the incident optical signal.

An electronics and processing subsystem includes a set of signal sources, an analog-to-digital conversion circuit, data acquisition circuitry, and a processor. The signal sources are configured and operative to generate respective ones of the RF modulation signals based on corresponding RF modulation command values from the processor. The analog-to-digital conversion circuit is configured and operative to generate respective streams of raw digital sample values from the analog detection signals, and the data acquisition circuitry and processor are co-configured and co-operative to:

(1) provide the RF modulation command values to the signal sources in synchronism with sampling operation of the analog-to-digital conversion circuit and according to an offset pattern and rate that includes stepping through an RF range for each of the RF modulation signals according to the model, using a predetermined step size, the stepping being performed at a sufficiently high rate to obtain measurements of the absorption value and the scattering value for each of the wavelengths in each of respective measurement intervals at least 10 times per second, and (2) in each of the measurement intervals, calculate the model to obtain one or more respective blood oxygen values from the respective measurements of the absorption values and scattering values of the measurement interval, and display or otherwise use the obtained blood oxygen values in higher-level diagnostic assessment of the blood oxygenation of the tissue.

Important aspects of the disclosed technique include orchestration of digital and analog hardware operation in the following manner:

Simultaneously control multiple (two or more) digital scannable frequency generators to act in concert to drive and modulate corresponding optical sources at offset modulation frequencies in an RF range, e.g., 50 to 400 MHz or higher (theoretically higher frequencies are possible, up to 1 GHz).

Time-synchronize to each digital frequency generator a two-channel analog-to-digital converter to collect a number (may be user defined) of digital samples of the measured signal. This synchrony happens with an accuracy of between 1,000 nanoseconds down to less than 1 nanosecond, depending on ADC sampling frequency. In one embodiment, the system can operate over a range of 1 MHz to 1.8 GHz, with the upper limit defined by currently available hardware. Each modulation frequency step is recorded within one known sampling period prior to the next increment in modulation frequency. This allows precise book-keeping of raw data from each wavelength/modulation frequency pair in stored memory.

The digital scannable frequency generators are programmed so that each wavelength is modulated through the full modulation frequency bandwidth (typically 50-400 MHz in 1-7 MHz steps). This requires that at least one digital frequency generator begin the sweep at a modulation frequency higher than the smallest modulation frequency values (in this case 50 MHz), and will therefore reach the largest modulation frequency (400 MHz) and wrap around to the lowest modulation frequency (50 MHz) to finish the full sweep.

One important feature of the system is that measurements from multiple optical sources are collected simultaneously over a broad modulation frequency range. In order to accomplish this, the system does not use narrow electrical (i.e. RF) bandpass filters centered on a single modulation frequency like in other works. Rather, the analog-to-digital converter allows collection of modulation frequencies over a broad modulation frequency range (e.g., 50-400 MHz). One disadvantage of this approach is that it allows for parasitic noise to be collected during digital conversion to a greater degree than band-passed single frequency systems. To overcome this issue, a more lengthy time-domain capture can effectively reduce the overall noise floor through process gain, in which the noise floor is reduced by a factor of 10 log(M/2) where M is the number of samples collected. If fewer samples are collected, then the noise floor begins to deteriorate the signal-to-noise of each optical signal. This creates a tradeoff between sample length (and better SNR) and acquisition speed (the fewer the samples, the faster the acquisition speed during a sweep). This highlights the importance and necessity of the simultaneous sweep paradigm. Since all optical sources are collected and swept simultaneously, multiwavelength data can be collected rapidly with sufficient SNR for tissue measurements. The high density of data collection enabled by this setup allows for multi-wavelength broad modulation frequency bandwidth measurements to be collected in a rapid fashion, allowing for extraction of optical properties and chromophore concentration (e.g. oxy and deoxyhemoglobin) during the cardiac cycle.

In one embodiment, the system measures arterial and venous oxygen saturation and perhaps other physiologic parameters. These parameters require optical measurement many times during the cardiac cycle. Human heart rate can vary over a wide range depending on age and disease state. For example, tachycardia is considered a heart rate >186 bpm in 3-5 month olds. We assume a max hear rate of 240 bpm. The required measurement rate required to extract arterial and venous oxygen saturation is not only dictated by the maximum heart rate however, as it is necessary to measure the difference between maximum and minimum hemoglobin levels during each heartbeat, and insufficient sampling may miss peaks. Many pulse oximeters operate with measurement rates of 500 Hz or greater in order to extract sufficient time-domain detail to determine arterial oxygen saturation. Overall, measurement rates in the range of 10 Hz to 500 Hz or higher are contemplated for the system 10.

The overall system measurement rate for this system is determined by the number of samples collected, the ADC sampling rate, and the range and number of modulation frequencies collected. In one embodiment, the following parameters are used: 250 MHz sampling frequency, sample length of 4096, sweep from 50-300 MHz in 7 MHz increments. This allows for an overall measurement rate of 97 Hz, sufficient to adequately sample the cardiac cycle for a physiological range of heat rates, determined by our initial normal volunteer measurements. This measurement rate can be substantially increased dependent on the measurement parameters (e.g. the number of samples can be reduced, with an in-kind reduction in SNR; the number of modulation frequencies can be reduced, but this may decrease measurement accuracy).

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views.

FIG. 4 is a mathematical description of a model relating amplitude and phase to coefficients of absorption and scatting;

DETAILED DESCRIPTION

Overview

Figure 1:
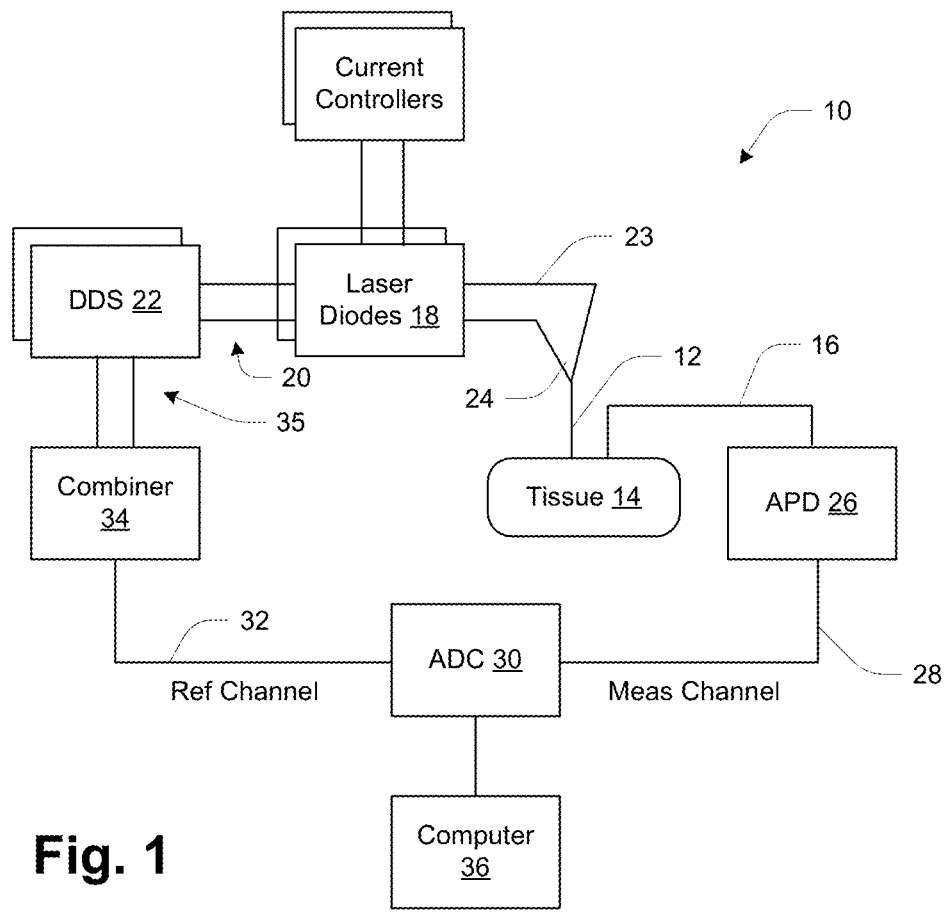
FIG. 1 is a functional block diagram of a tissue oximetry system.

The new technology described herein may address unmet needs and limitations of current pulse oximetry by providing new, highly quantitative information about both arterial and venous oxygen saturation, as well as providing quantitative tissue-level concentrations of oxygenated and deoxygenated blood, total blood volume, as well as timing information related to the cardiac cycle. The disclosed technology may be implemented in a wide variety of hospital settings representing broad patient impact, including but not limited to continuous monitoring in the intensive care unit, rapid diagnostics related to shock or pulmonary embolism, diagnosis and treatment evaluation of diabetic peripheral vascular disease, and evaluation of abnormal blood flow in tumors. The disclosed technology has the potential to impact or replace pulse oximetry and fiber optic pulmonary artery catheters measuring $SvO_2$.

Disclosed are apparatus and methods for non-invasive continuous monitoring of oxygenation, referred to as High Speed Quantitative Tissue Oximetry. The oximetry technique is designed to provide new and important information about tissue and organ perfusion, oxygenation, cardiac fitness, and overall tissue health and viability through optical and non-invasive means. The new tissue oxygenation metrics provided by the disclosed technique, which include total blood volume, oxy- and deoxyhemoglobin concentrations in the arterial and venous components, pulse transit times related to cardiac timing, and venous oxygen saturation ($SvO_2$), have the capability of disrupting the current standard-of-care in areas including critical care monitoring, diagnosis of vascular diseases, shock, and diagnosis, prognosis, and treatment monitoring of solid tumors.

As described herein, the oximetry technique may employ ultra-fast frequency-domain diffuse optical spectroscopy (FD-DOS) to obtain multi-wavelength determinations of tissue optical properties with a sufficient measurement rate to capture pulsatile changes throughout the cardiac cycle. This allows for the extraction of new quantitative hemodynamic parameters that significantly extend the capability of traditional pulse oximetry and co-oximetry, both of which are ubiquitous medical technologies but which are limited by the ability to measure only arterial oxygenation, and often rely on considerable assumptions that may cause unacceptable measurement errors in many situations.

Measurements are non-invasive and can be taken with a handheld probe, clip (similar to current pulse oximetry devices), or other tissue-contact probes and digital electronics are used to capture and analyze measurements. The technology has the potential to be implemented in all current clinical situations in which pulse oximetry or catheter based oxygen sensing is conducted, which includes almost all bedside monitoring systems.

Additionally, the system may be capable of flexible configuration, such as providing for user or application definition of modulation frequency range and/or step size. In this respect, different tissues (with corresponding different optical properties) may benefit from being measured with different ranges of modulation frequencies. Thus for one type of tissue, using a larger modulation bandwidth (e.g. 50-400 MHz) is needed to provide high accuracy in the optical property estimate, whereas for other tissues a smaller bandwidth (e.g. 50-100 MHz) may work just as well. There may also be a dependence of the number of different modulation frequencies used for a given frequency range (50:1:400 versus 50:5:400) on optical property accuracy that is again, tissue dependent. Thus, the pattern of modulation frequencies may be tailored to match the tissue type, to optimize optical property estimation accuracy, while reducing the collection of unnecessary data. This capability arises from the use of electronics that dynamically control both the modulation frequency sources as well as the sampling circuitry while performing correct bookkeeping to match stimulation frequency with the collected data stream.

DESCRIPTION OF FIGURES

FIG. 1 shows a tissue oximetry system 10 employing frequency-domain diffuse optical spectroscopy (FD-DOS). In operation it directs an incident optical signal 12 to an in vivo tissue 14, and it processes a detected optical signal 16 that results from absorption and scattering of the incident optical signal by the tissue 12. The processing provides measurements of blood oxygen values for blood flowing in the tissue 14, as described more below. In general the tissue 14 may be any accessible tissue, such as an external skin surface (e.g., fingertip, earlobe, etc.), or an internal tissue which has been made accessible such as by an incision, etc. as during a surgery. Placement of optical source(s) and detector(s) may vary in different embodiments, depending on a variety of factors as generally appreciated in the art.

More particularly, the system includes a set of optical sources 18 shown as laser diodes, which have respective distinct wavelengths and are intensity-modulated by respective RF modulation signals 20 from respective direct digital synthesizers (DDSs) 22. Modulated optical signals 23 from the lasers 18 are combined by a fiber combiner 24 to generate the incident optical signal 12 directed to the tissue 14. The system includes one or more optical detectors 26, shown in FIG. 1 as an avalanche photodiode (APD), that generate analog detection signal(s) 28 indicative of amplitude and phase of RF modulation components of the detected optical signal 16. The analog detection signal 28 from APD 26 is shown as a measurement channel input to an analog-to-digital converter (ADC) 30. Analogously, a reference channel input 32 is formed by a combiner 34 which receives counterparts 35 of the RF modulation signals 20 from the DDSs 22. The ADC 30 performs high-speed sampling and conversion of the analog measurement signal 28 and reference signal 32 to corresponding streams of digital samples, which are provided to a computer 36 for processing as described herein.

Generally, the system 10 performs FD-DOS operations as follows to obtain an estimate of one or more blood oxygen values, such as arterial or venous oxygen saturation. In some embodiments, operation may be repeated indefinitely in successive intervals referred to as "measurement intervals" or MIs. Within a measurement interval, the modulation of the laser diodes 18 is swept across a predetermined RF frequency range, such as from 50-400 MHz for example, and the resulting modulated optical signals 23 are combined and directed to the tissue 14 as the incident optical signal 12. This signal is both attenuated and scattered within the tissue 14, producing the detected optical signal 16 which includes components at each of the modulation frequencies. The detector 26 generates a baseband analog detection signal 28 that carries the modulation components, and this signal is sampled at a high rate by the ADC 30 (along with sampling of the reference signal 32). In particular, a large number of samples is obtained for each set of modulation frequencies, and each set of samples is processed into a frequency-domain representation in order to readily obtain amplitude and phase responses at each of the modulation frequencies. In general, a Fourier transform type of approach may be used, but a more optimized approach includes use of a so-called Goertzel filter, which can efficiently recover signals of known frequencies (in this case, the modulation frequencies). The system assumes a model of optical response of the tissue 14 based on concentration of hemoglobin species, and an inverse of this model is applied to the measured response as provided by the frequency-domain processing in order to estimate actual species concentrations, from which the tissue oxygenation measures are obtained. These details are described below.

Figure 2:
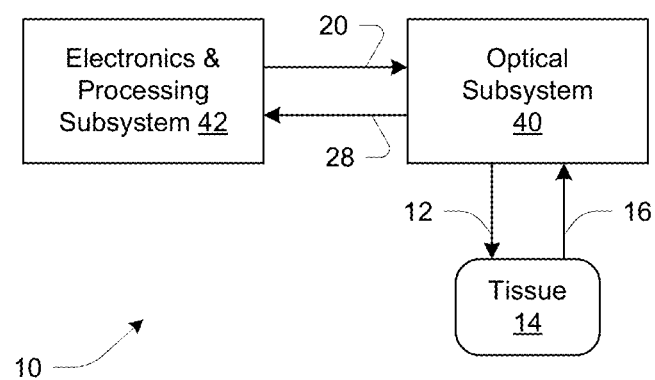
FIG. 2 is a generalized block diagram of the tissue oximetry system.

FIG. 2 is a generalized depiction of the system 10 as including an optical subsystem 40 and an electronics and processing subsystem 42. As described more below, the optical subsystem includes the optical components shown in FIG. 1 such as the lasers (sources) 18, fiber combiner 24, and detector (APD) 26, while the electronics and processing subsystem 42 includes the DDSs 22, ADC 30 and other electronic components as well as the computer 36 and other processing circuitry. The electronics and processing subsystem 42 may have a network connection or similar external data connection (not shown) for communicating with separate systems such as a higher-level controller and/or other computers. Values measured by the system 10 may be provided to such external systems for specific uses such as incorporating into a diagnostic assessment, displaying information to remote users, etc.

Figure 3:
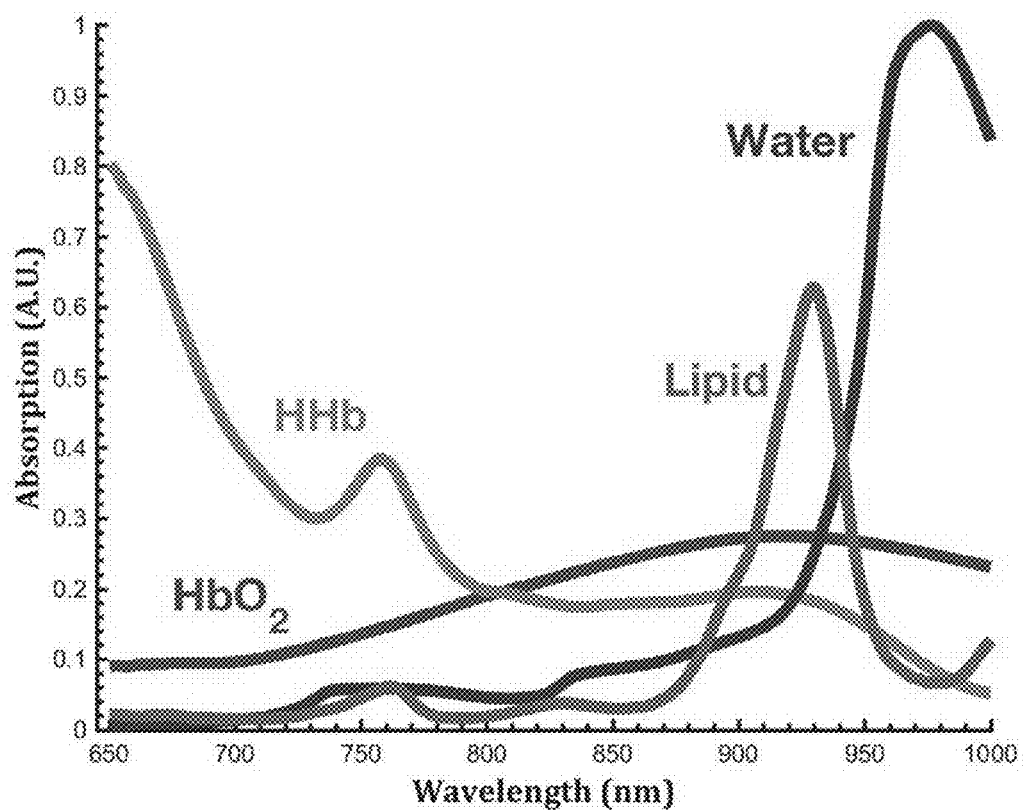
FIG. 3 is a plot of absorption versus wavelength for a variety of chromophores according to a model.
Figure 5:
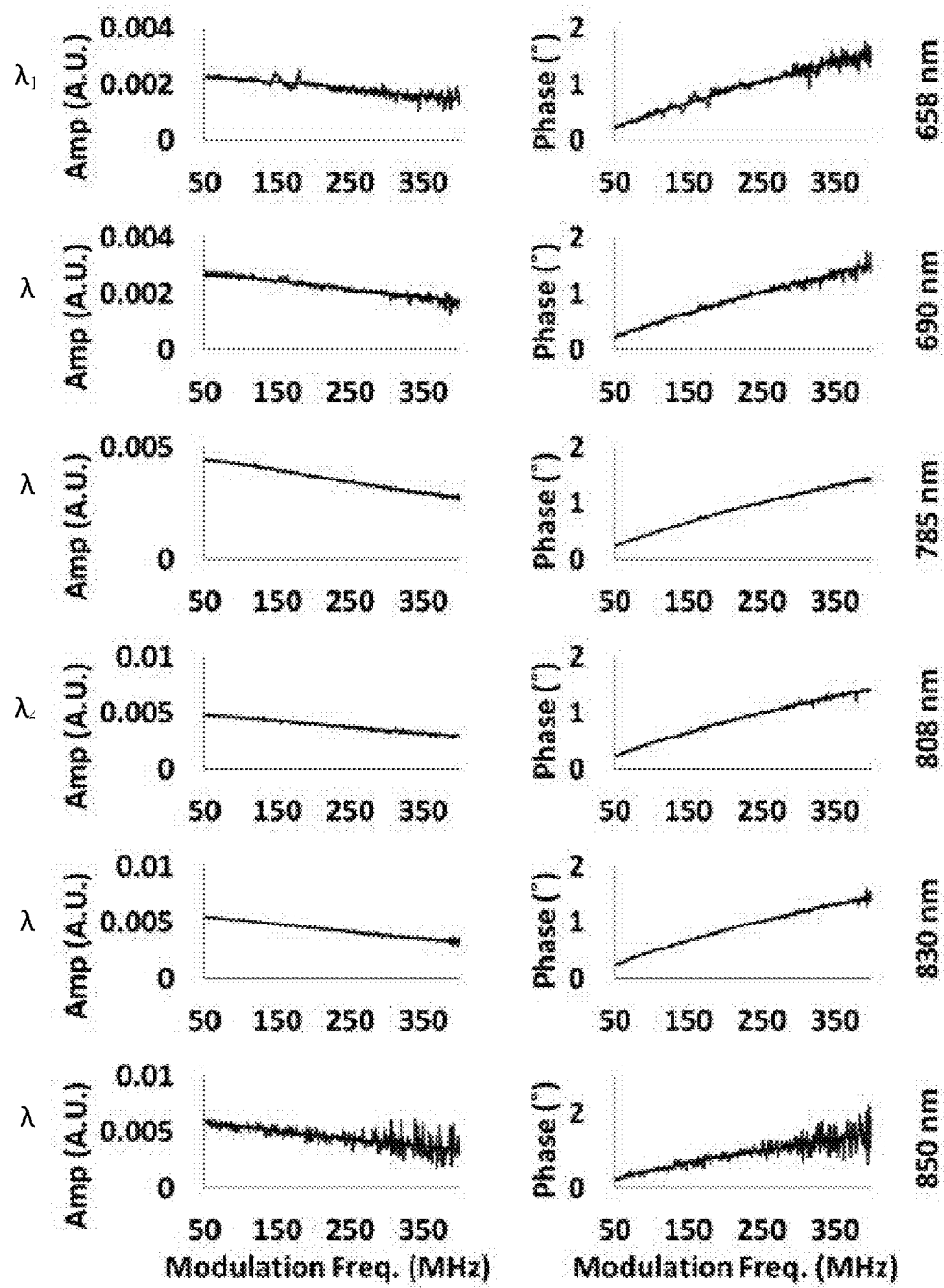
FIG. 5 is a set of plots of amplitude and phase of modulation components of a detected optical signal.

FIGS. 3-5 describe aspects of a high-level model for the interaction of modulated light with biological tissue, which provides an analytical basis for obtaining estimates of blood oxygen values from measurements of optical response as described herein. In alternative embodiments, other modeling approaches may be used, including for example models based on machine learning, system identification, neural networks, etc.

FIG. 3 presents a set of plots that model the relationship between an absorption-versus-wavelength characteristic and respective values of certain substances, namely oxyhemoglobin (shown as $O_2Hb$), deoxyhemoglobin (shown as HHb), water ($H_2O$), and lipid. Such substances that interact with incident light in particular ways are also termed "chromophores" herein.

FIG. 4 presents an example diffusion model that relates measured amplitude attenuation and phase lag values (Aatt and Φlag) to absorption and scattering coefficients $\mu_a$ and $\mu_s'$, via certain constants shown as $k_{real}$ (real component) and $k_{imag}$ (imaginary component). This model can be used in inverse form to obtain measured values for absorption, and the absorption values for multiple wavelengths can be used to obtain chromophore concentration based on the model of FIG. 3.

FIG. 5 shows a set of plots of values obtained by system operation, from which the values for $k_{real}$ and $k_{imag}$ (FIG. 4) are obtained for use in solving the inverse model as described above. Plots are shown of amplitude and phase measured for modulation signals swept across a range from 50 to 400 MHz in steps of 1 MHz, for each of a set of wavelengths $\lambda_1$-$\lambda_6$. The value $k_{imag}$ (FIG. 4) is proportional to the slope of the phase plot, while $k_{real}$ (FIG. 4) is proportional to the log of the slope of the amplitude plot.

Figure 6:
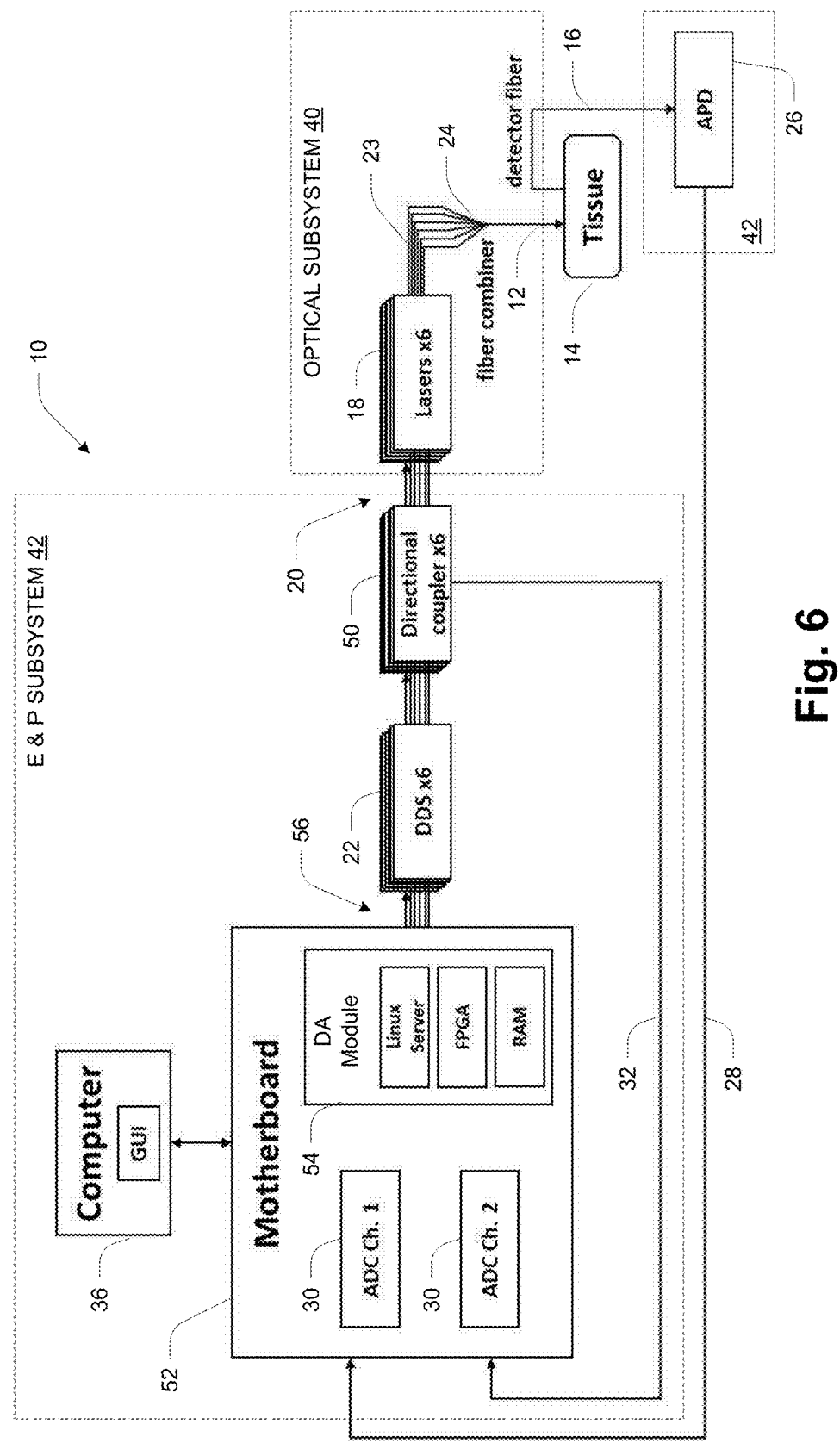
FIG. 6 is a schematic diagram of a tissue oximetry system according to one embodiment.

FIG. 6 shows the system 10 with a particular embodiment of the electronics and processing (E & P) subsystem 42. It includes the DDSs 22 as well as directional couplers 50, and a motherboard module 52 containing the ADC circuitry 30 as well as a data acquisition (DA) module 54. In one embodiment the DA module 54 includes random-access memory (RAM) for storing data from the ADC 30, an FPGA providing high-speed hardware-level control, and a processor for overall control and execution of certain tasks including the transfer of data between the motherboard 52 and computer 36. The processor may be realized as a so-called ARM (advanced RISC machine) processor, and typically executes a kernel such as a Linux server. The DDSs 22 and directional couplers 50 together generate the RF modulation signals 20 by digital synthesis and digital-to-analog conversion based on corresponding RF modulation command values 56 from the DA module 54. The ADC circuitry 30 generates respective streams of raw digital sample values from the analog detection signals 28 and provides those digital sample values to the DA module 54 for storage and transfer to the computer 36. The directional couplers 50 provide the reference signal 32 used for normalization of sensed amplitude and phase values in processing. In operation, the DA module 54 generates the RF modulation command values 56 in synchronism with the acquisition of the digital sample values from the ADC circuitry 30, as described more below.

In one embodiment each DDS 22 can output up to 20 mA of current modulated at frequencies as high as 400 MHz. The RF output of each DDS 22 may be low-pass filtered at 400 MHz and routed to the respective directional coupler 50 which sends the majority of the output power to a respective laser 18. A lesser output from each directional coupler 50 is routed to a power combiner (item 34 in FIG. 2; not shown in FIG. 6) whose output serves as the reference signal 32 sent to channel 2 of the ADC circuitry 30. The lasers 18 may be implemented with near infrared (NIR) laser diodes with wavelengths of 658, 690, 785, 808, 830, and 850 nm in one example. The laser diodes 18 are coupled to the fiber combiner 24 which may be realized as 400-µm core diameter fibers bundled into a single ferrule. Each laser diode 18 is driven with a DC current, which is mixed with an RF current using a bias-tee (not shown) to intensity-modulate the light. DC current is supplied by an 8-channel, high-stability laser diode controller (not shown).

In the illustrated embodiment the system 10 uses six individual DDSs 22 to simultaneously modulate a bank of laser diodes 18 at offset modulation frequencies. The multiplexed modulation signals are decoupled in the frequency domain in post processing, as described more below. A typical measurement, for example, may sweep through frequencies between 50 and 400 MHz in steps of 1 MHz with the modulation frequency for each wavelength offset by 10 MHz, as described more below. This multiplexing helps reduce measurement duration, to less than 100 ms per frequency sweep for example, allowing for detection of rapid physiological changes. In examples herein, operation with modulation frequencies between 50 and 300 MHz or between 50 and 400 MHz are described. The frequency step size can be set to other values, generally between 1 MHz and 7 MHz. For high-speed measurements, 7 MHz steps may be chosen to optimize the temporal resolution of frequency sweeps, while for slower measurements 1 MHz steps may be chosen to improve frequency resolution.

The optical combiner 24 is especially useful if an optical fiber is used to bring the incident light to the tissue 14. Alternatively, a probe could be constructed with light sources (e.g., miniature lasers) and detectors directly on the tissue, in which case an optical combiner wouldn't be needed the sources could be physically adjacent to each other and the incident optical signal 12 formed by natural combining of the output signals within the tissue 14.

Figure 7:
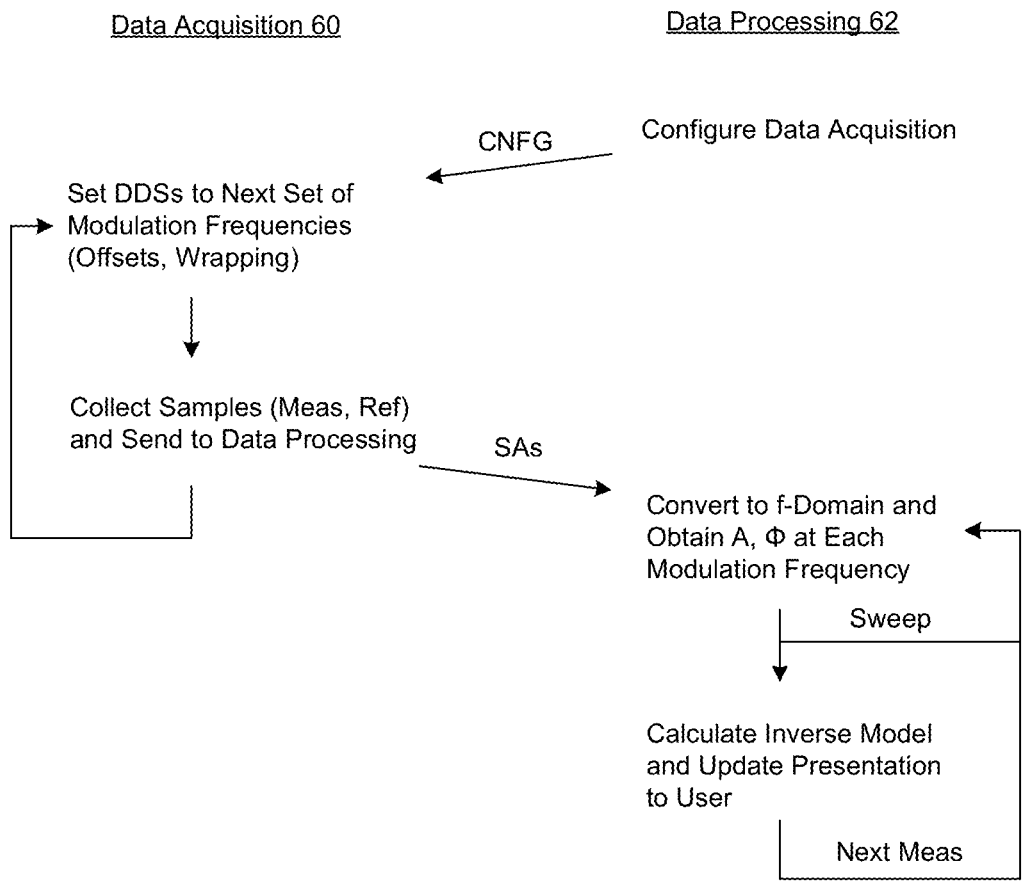
FIG. 7 is a flow diagram depicting aspects of operation at a high level.

FIG. 7 depicts operation of the E & P subsystem 42 at a high level, divided into data acquisition operations 60 (generally performed by DA module 54) and data processing operations 62 (generally performed by computer 36). Initially, the data processing 62 configures the data acquisition process 60 in a desired manner, including for example by programming modulation frequencies into the DDSs 22, establishing the number of samples to be collected per frequency step, etc. The data acquisition process 60 is essentially a sequence of sample collection intervals, each including first setting the DDSs 22 to generate a next set of modulation frequencies, then collecting a set of samples of the reference and measurement signals 32, 28 with the lasers 18 so modulated. The sample length is selected to provide a desired level of "processing gain", which is explained more below. In some embodiments the sample length may be 1 k, 2 k, or 4 k for example.

Once a set of samples is collected and stored in the DA module 54 for a given set of modulation frequencies, two things happen. First, the data acquisition process 60 iterates to perform the same sampling operation on a next set of modulation frequencies. In parallel, the samples (SAs) are provided to the data processing 62 for processing. In the embodiment of FIG. 6, this transfer of SAs occurs between the memory of the DA module 54 and the computer 36.

Subsequent data processing 62 is shown as having two major components. First, each set of samples is processed into the frequency domain (F-domain) where values are obtained for the amplitude (A) and phase (Φ) for each modulation frequency. These values are stored in association with the specific source wavelengths to which the respective modulations are applied. This is explained more below. The term "sweep" in FIG. 7 indicates that this step is repeated for each set of samples obtained for one sweep across the full range of modulation frequencies, thereby obtaining amplitude and phase values for all modulation frequencies for all wavelengths. Thus one sweep corresponds to many iterations of the above-described sample-collection operation of the data acquisition process 60. Once such a sweep is done, the data processing 62 uses the set of amplitude and phase values to solve an inverse model (as described above) and thereby obtain values which are estimates of blood oxygen values. These values are used as dictated by the specific operating environment for the system 10. In one example, the system 10 may be realized in a monitoring device that continually presents (e.g., via a display) indications of the blood oxygen values to an external user. Such operation is indicated in FIG. 7 as "update presentation to user". The two operations of the data processing 62 are referred to herein as a "measurement", and each period in which they occur is termed a "measurement interval". In an example embodiment, measurement intervals are repeated in succession indefinitely, which is indicated as a "next meas" iteration in FIG. 7.

Figure 8:
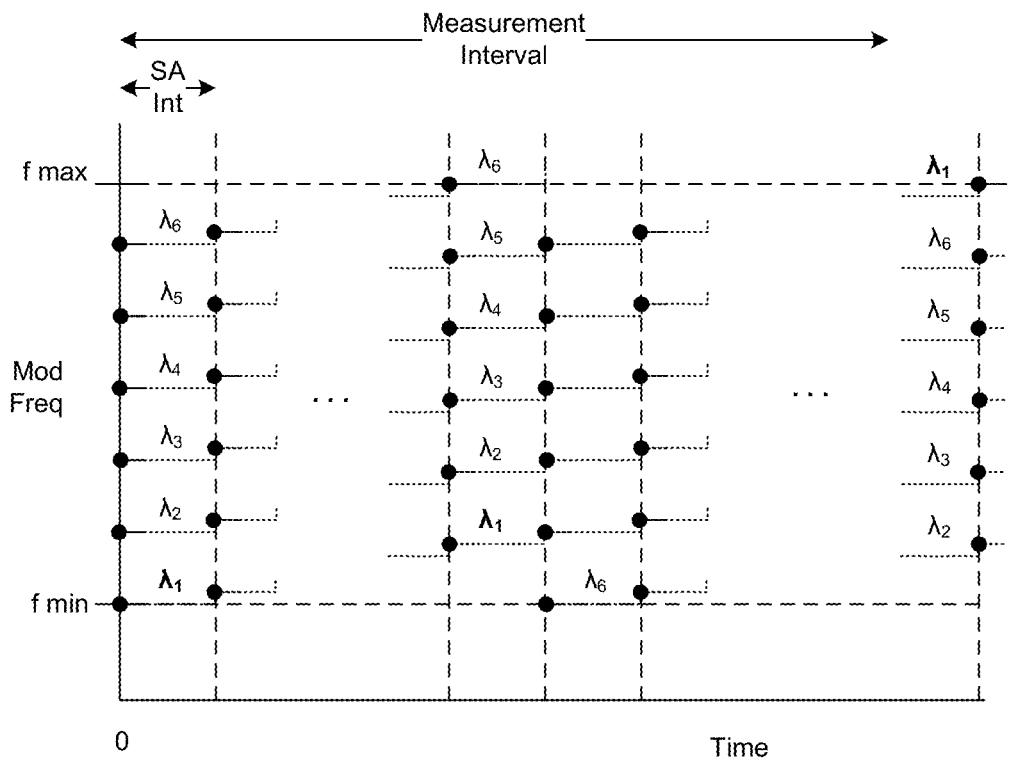
FIG. 8 is a schematic representation of a scheme for swept modulation of a set of optical signal over a measurement interval.

FIG. 8 illustrates the setting and sweeping of modulation frequencies in a measurement interval, which consists of a sequence of sample intervals (SA INT) as described above. At time 0, an initial set of offset modulation frequencies is generated by the DDSs 22 and applied to the lasers 30. In FIG. 8, each modulated optical signal from a respective laser is indicated as $\lambda_x$, with x ranging from 1 to 6 in this example. This plot roughly illustrates an example of 10 MHz offset with 1 MHz steps. As shown, for $\lambda_1$, the modulation frequency sweeps monotonically from the minimum modulation frequency (fmin) to the maximum (fmax) over the measurement interval. For the other optical signals, the modulation frequency wraps around from fmax to fmin at some point during the sweep. This is illustrated for $\lambda_6$, which in this example is the first signal to wrap.

During this process, the analog-to-digital converter 30 acquires time-domain samples in synchrony with the stepping of the modulation frequencies, collecting data so it can be analyzed in the frequency domain. For coherent operation in collecting and storing the frequency-encoded optical information, the timing of the DDSs 22 and the analog-to-digital converter 30 is controlled to within 1 digital sampling period, which is defined by the sampling frequency of the ADC 30. In some embodiments, a range of sampling frequencies from 1 MHz to 1.8 GHz is theoretically feasible, requiring timing accuracy between 1,000 nanoseconds and 0.5555 nanoseconds respectively. For a sampling rate of 250 MHz, the timing accuracy is 4 ns. After the data is stored, it is sorted and analyzed to extract amplitude dampening and phase delays induced by the tissue 18. The high density of data collection enabled by this setup allows for multi-wavelength broad modulation frequency bandwidth measurements to be collected in a rapid fashion, allowing for extraction of optical properties and chromophore concentration (e.g. oxy and deoxyhemoglobin) during the cardiac cycle.

Figure 9:
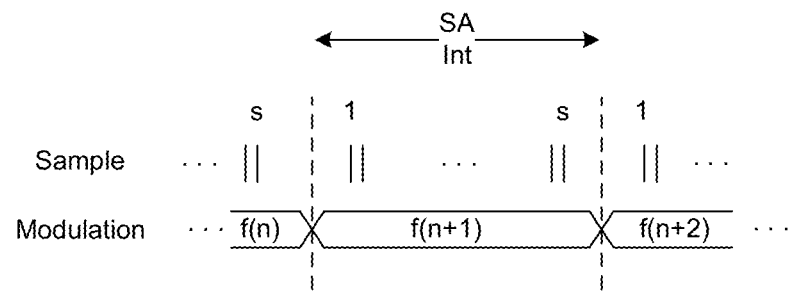
FIG. 9 is a timing diagram showing a timing relationship between sampling and frequency transitions.

FIG. 9 illustrates the timing relationship between sampling and the transitions or steps of the modulation frequencies. The set of samples in a sampling interval are indicated as 1 . . . s. Two steps of the modulation frequencies are shown, f(n) to f(n+1) and f(n+1) to f(n+2). Successive transitions bound the sample interval, and each set of samples 1 . . . s occurs between successive transitions as shown. Given the hardware-level control of the DDSs 22 and collection of samples from the ADC 30, a very fast transition can be made between the completion of the last sample s for a given interval and the first sample 1 for the next interval, limited only by the time required for the DDSs 22 to transition to the next frequency and for that transition to propagate through the lasers 30, tissue 18, and detector 34. The transition does not involve execution of higher-level software or use of relatively show communications between the DA module 54 and the computer 36.

Figure 10:
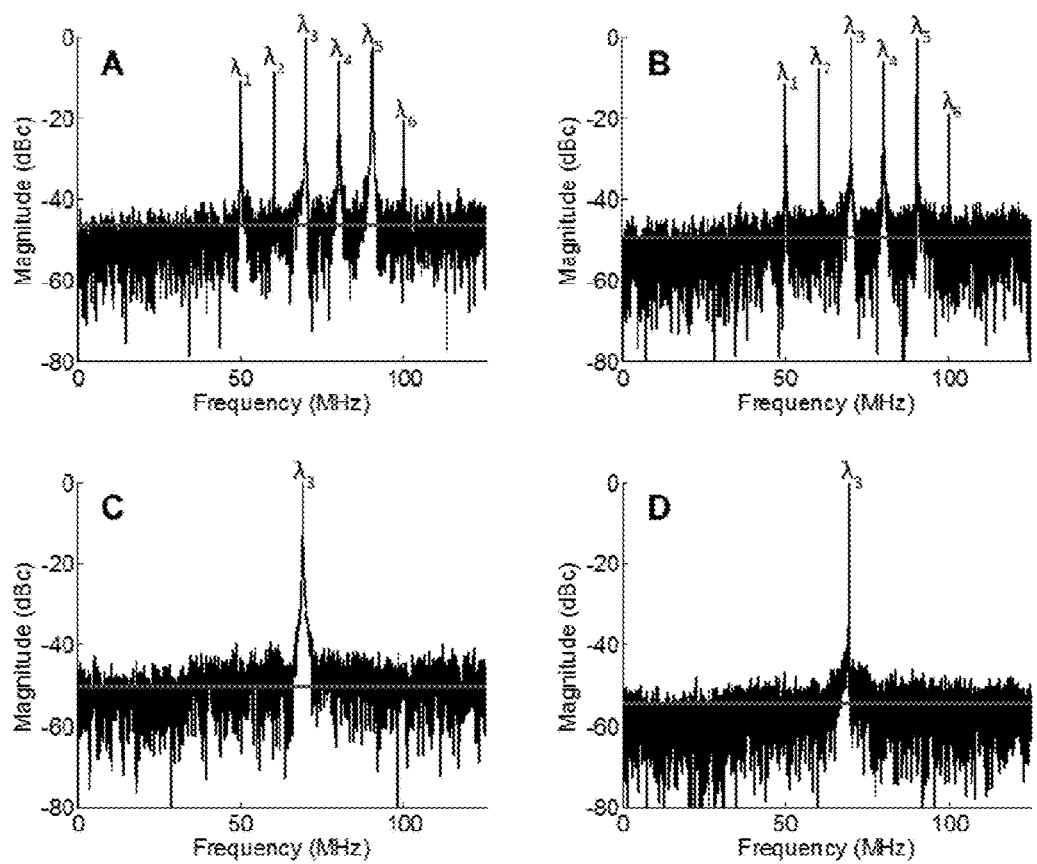
FIG. 10 is set of plots of frequency domain data showing signal to noise performance.

FIG. 10 illustrates example signal to noise ratios and the concept of process gain used in the system. In these plots of frequency domain data, each modulation frequency appears as a spike with a label for the corresponding modulated wavelength. Plot A shows the detected modulation components for six wavelengths modulated simultaneously with 4096 samples obtained acquired per frequency step. This example exhibits a noise floor of 46 dBc (dB below "carrier", in this case the amplitude of the modulation signal for $\lambda_3$). Plot B shows results for six wavelengths modulated simultaneously with 8192 samples acquired per frequency step. In this case the noise floor is lowered to 49 dBc. Plot C shows results for a single 785 nm laser modulated at 70 MHz with 4096 samples acquired. The noise floor is 50 dBc. Plot D shows results for a 785 nm laser modulated individually at 70 MHz with 8192 samples acquired, with a lower noise floor of 54 dBc.

One important feature of the disclosed technique is that measurements from multiple (two or more) optical sources are collected simultaneously over a broad modulation frequency range. In doing so, the system does not use narrow electrical (i.e. RF) bandpass filters centered on a single modulation frequency as has been done in other systems. Rather, the analog-to-digital converter 30 allows collection of modulation frequencies over the entirety of a broad modulation frequency range (e.g., 50-400 MHz). This allows for parasitic noise to be collected during digital conversion to a greater degree than in bandpass single frequency systems. To overcome this issue, an extended time-domain capture can effectively reduce the overall noise floor through process gain, in which the noise floor is reduced by a factor of $10 \log(M/2)$ where M is the number of samples collected. FIG. 10 shows this noise floor after fast Fourier Transforms of 4096 and 8192 sample lengths. If fewer samples are collected, then the noise floor begins to deteriorate the signal-to-noise of each optical signal. This creates a tradeoff between longer sample length (and better SNR) and faster acquisition speed (shorter sample length provides for faster acquisition speed during a sweep). It also highlights the importance of the simultaneous sweep paradigm described herein. Since all optical sources are collected and swept simultaneously, multi-wavelength data are collected rapidly with sufficient SNR.

Additional Specifics

Below there is description of additional specific features that may be incorporated into embodiments.

1. Detection

In one embodiment, a reflectance mode geometry is used for the measurements, with the source fiber from combiner 24 and the active area of the detector 26 placed directly on the surface of the tissue 14 using a suitable source-detector separation (e.g., 5 mm to several cm). In one embodiment an APD detector 26 is used having 0.5 mm active area, 2.50× $10^5$ V/W photoelectric sensitivity, and a high band cutoff of 1 GHz. It may contain its own bias power supply and low-noise amplifier within a compact package.

In one embodiment the ADC circuitry 30 employs a 14-bit, 2-channel ADC with a 2 V peak-to-peak full scale input voltage to sample the signal at each channel at 250 mega-samples per second (MSPS). The electrical output of the APD detector 26 may be high-pass filtered at 41 MHz and routed to the first channel of the ADC circuitry 30, while the combined reference signal from the directional couplers 50 is routed to the second channel of the ADC circuitry 30. At each frequency step, the ADC circuitry 30 collects 4096 samples on each channel. If a lower noise floor is desired, more samples can be collected (e.g. 8192, 16384 . . . 2n), but increasing the number of samples per step substantially increases both the required data transfer rates as well as processing time. Both channels of the ADC circuitry 30 can run off of the same clock and be sampled simultaneously.

2. Signal Processing

Signal processing may be performed using a tissue oximetry application executed in the computer 36. An undersampling technique may be used. With an ADC sampling rate of 250 MSPS, all signals modulated above 125 MHz are aliased. Given that the modulation frequency is known for each wavelength at each frequency step, the signal of interest is easily located in the baseband. The processing algorithm eliminates modulation frequencies that are multiples of the Nyquist frequency, then maps all measured (aliased) frequencies in the baseband to the corresponding original modulation frequencies. The algorithm also removes any measurements in which multiple wavelengths are aliased to the same frequency in the baseband (i.e. signals at 120 and 130 MHz are both read as 120 MHz and eliminated).

A fast Fourier transform (FFT) with a rectangular window may be used at each frequency step to calculate the amplitude and phase for the reference and sample channels. The appropriate frequency bin is located for each wavelength at each modulation frequency step. The magnitude of the FFT of the measurement channel relative to that of the reference channel is considered the raw amplitude value, and, similarly, the phase offset between the measurement and reference channels is considered the raw phase value. As noted above, a more efficient technique is the Goertzel algorithm.

3. Measurement Calibration

The raw amplitude and phase represent the amplitude attenuation and phase delay induced both by the tissue and the instrument. In order to remove the instrument response, a measurement can be taken on an object with known optical properties. In one example, a silicone object referred to as a "phantom" can be used. As a forward model, an approximation of the Boltzman transport equation with boundary conditions for semi-infinite geometry can be employed. Calibration factors for amplitude and phase can be determined by ratiometrically or differentially comparing measured amplitude and phase, respectively, to theoretical amplitude and phase from the forward model. These calibration factors are then applied to the subsequent raw amplitude and phase measurements in order to obtain calibrated amplitude and phase.

4. Optical Property and Chromophore Recovery

A fitting algorithm (e.g., iterative least-squares) can be employed to fit the forward model calculated and measured calibrated amplitude and phase in order to extract absorption ($\mu_a$) and scattering ($\mu_s'$) parameters at each wavelength. Chromophore extinction coefficients are obtained, and a modified version of Beer's Law (FIG. 3) can be used to extract chromophore concentrations from multi-wavelength $\mu_a$ data.

5. Speed

The tissue oximetry system 10 utilizes wavelength multiplexing, which eliminates switching time between lasers and reduces data acquisition time, resulting in the ability to measure fast physiological changes. The rate at which frequency sweep measurements can be performed is dependent on the range of modulation frequencies, the number of discrete steps used, and the number of samples acquired at each frequency step, as well as the data transfer and processing rates. In one embodiment, multiplexing six laser wavelengths, sweeping from 50 to 300 MHz with 7 MHz steps, and acquiring 4096 samples per frequency step, the maximum measurement rate is dependent in part on the processing throughput. In one example, an overall measurement rate is greater than 10 Hz, and in particular can be as high as 100 Hz. Increasing the frequency sweep range to 50 to 400 MHz may reduce the measurement rate, e.g., to about 68 Hz. When decreasing the frequency step size to 1 MHz, the 50 to 300 MHz sweep can be acquired at about 14 Hz and the 50 to 400 MHz sweep can be acquired at about 10 Hz. These measurement speeds allow for FD-DOS data acquisition that can capture fast physiological changes, including during the cardiac cycle.

Cuff Occlusion Test

Figure 11:
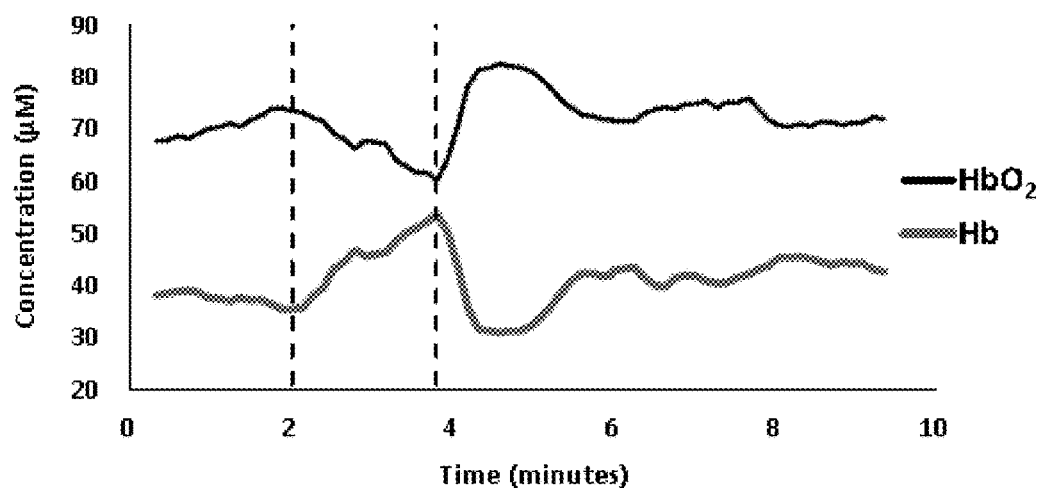
FIG. 11 is a plot of measured hemoglobin concentrations versus time for a cuff occlusion test.

FIG. 11 shows measurements of oxyhemoglobin ($HbO_2$) and deoxyhemoglobin (Hb) concentrations obtained over time during a in vivo cuff occlusion experiment in which a blood pressure cuff was placed on the upper arm of subject while optical measurements were taken on the forearm. The cuff was loosely secured in order to measure baseline levels of Hb and $HbO_2$, then inflated to 200 mmHg for approximately 2 minutes. The cuff was released and data were acquired for approximately 5 additional minutes. Frequency sweeps between 50 and 400 MHz, with frequency steps of 7 MHz, were used to modulate all 6 laser diodes simultaneously. Measurements were taken approximately every 8 seconds for nearly 10 minutes. The source-detector separation was 15 mm, and chromophore concentrations were calculated for oxy-, deoxy- and total hemoglobin for each measurement.

FIG. 11 shows $HbO_2$ and $Hb$ concentrations throughout the cuff occlusion test. At baseline the average oxy- and deoxyhemoglobin concentrations were 67.6 and 38.1 μM, respectively. At the time of cuff release, oxyhemoglobin concentration had dropped to 59.9 μM and deoxyhemoglobin had increased to 52.2 μM. After cuff release oxyhemoglobin rebounded to a local maximum of 82.5 μM and deoxyhemoglobin dropped to 30.9 μM, before both chromophore concentrations began to return toward their baseline values. These results are consistent with reduced arterial supply and vascular drainage during cuff occlusion, followed by a rush of arterial blood into the forearm after cuff release.

Rapid In Vivo Measurements

Figure 12:
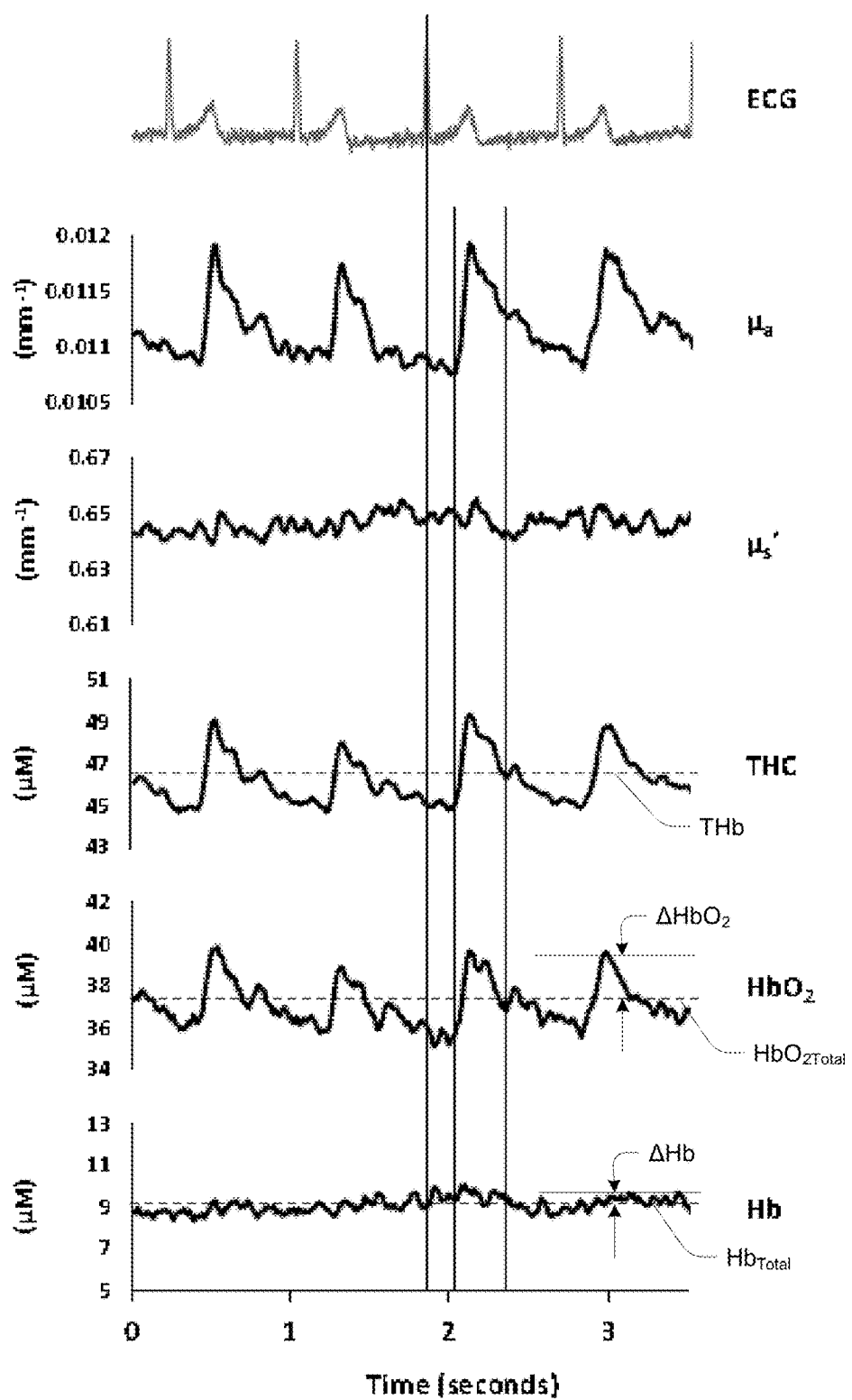
FIG. 12 is a set of plots of several values in an example use of the disclosed system, annotated to show total (T) and differential (Δ) values.

FIG. 12 shows results from another experiment in which measurements by operation in reflectance mode on the thumb of a subject, with 10 mm source-detector separation. These results show the ability of the tissue oximetry system 10 to measure physiological changes at or above the cardiac rate. Frequency sweeps from 50-300 MHz with 7 MHz steps were used to modulate all 6 laser diodes simultaneously. 350 frequency sweeps were taken with a measurement rate of 97.2 Hz.

An electrocardiogram (ECG) signal was measured simultaneously with the optical signal and synced using an external data acquisition board. FIG. 12 shows 5-point moving averages of the absorption ($\mu_a$) and reduced scattering ($\mu_s'$) coefficients and the concentrations of total, oxy- and deoxy-hemoglobin from the high-speed finger measurement, temporally aligned with the ECG signal. The $\mu_a$ values fluctuate temporally with the ECG signal, likely due to increased blood volume in the finger after ventricular contraction, whereas there is substantially less variation in $\mu_s'$ throughout the cardiac cycle. Similarly, total and oxyhemoglobin concentrations vary temporally with the ECG signal, while deoxyhemoglobin concentration shows minimal fluctuation throughout the cardiac cycle. Vertical dashed lines mark the peak of the ECG R wave, the start of the upstroke of the pulsatile waveform, and the dicrotic notch. There is a lag in the upstroke of the $\mu_a$ signal after the R-wave of the ECG, given the transmission time to the peripheral vasculature, which has been shown to range between 200 to 300 ms for photoplethysmographic signals measured in the fingertip. The dicrotic notch, which is correlated with end of the systolic ejection period, typically appears roughly 300 ms after the upstroke of the pulsatile waveform, correlating with the dip in $\mu_a$, total hemoglobin and oxyhemoglobin marked by the rightmost vertical line. Fluctuations in $\mu_a$, total hemoglobin and oxyhemoglobin appear to occur at the same frequency as the ECG signal, showing that tissue oximetry system is capable of detecting pulsatile, oxygenated, arterial blood flow.

Below are shown strategies for calculating blood oxygenation values (and in particular, venous $O_2$ saturation $SvO_2$), which are made possible by the ability to quantitatively measure the Hb parameters throughout the cardiac cycle. It should also be noted that measurements can be taken from multiple points on/in the body simultaneously, which may be useful for calculating $SvO_2$ or other parameters within a given region or compartment of the body.

The following terms are used below (* indicates measured values):

$HbO_{2A}$=arterial oxyhemoglobin [ ]
$Hb_A$=arterial deoxyhemoglobin [ ]
$HbO_{2V}$=venous oxyhemoglobin [ ]
$Hb_V$=venous deoxyhemoglobin [ ]

$$*Hb_{Total}=Hb_A+Hb_V$$

$$*HbO_{2Total}=HbO_{2A}+HbO_{2V}$$

$$*THb=HbO_{2A}+HbO_{2V}+Hb_A+Hb_V$$

$$*StO_2=HbO_{2Total}(HbO_{2Total}+Hb_{Total})=HbO_{2Total}/THb$$

$$*SaO_2=HbO_{2A}/(HbO_{2A}+Hb_A)=\Delta HbO_2/(\Delta Hbo_2+\Delta Hb)$$

$$SvO_2=(HbO_{2V})/(HbO_{2V}+Hb_V)$$

It is desired to obtain $SvO_2$, which can be related to cardiac output/activity. Currently, this value is measured using an invasive catheter. An approach like the following is used to solve for $SvO_2$ in terms of values that can be measured by the disclosed FD-DOS system.

$$SvO_2=(HbO_{2V})/(HbO_{2V}+Hb_V)=(HbO_{2Total}-HbO_{2A})/(HbO_{2Total}-HbO_{2A}+Hb_{Total}-Hb_A)$$

$$SvO_2=(HbO_{2Total}-HbO_{2A})/(THb-HbO_{2A}-Hb_A)$$

In the above, the term $Hb_A$ is replaced with an expression in terms of $SaO_2$ and $HbO_{2A}$:

$$SaO_2=(HbO_{2A})/(HbO_{2A}+Hb_A)$$

$$Hb_A=(HbO_{2A})/(SaO_2)-(HbO_{2A})$$

Thus:

$$SvO_2=(HbO_{2Total}-HbO_{2A})/(THb-HbO_{2A}/SaO_2)$$

$$SvO_2=(HbO_{2Total}*-HbO_{2A})/(THb*-(HbO_{2A}/SaO_2*))$$

An estimate is needed for $Hbo_{2A}$, because it is not measured directly. For this, a value x is introduced:

$$x=THb_V/THb$$

and the remaining results are given in terms of x. In many situations a good estimate of x is 0.75, i.e., $THb_V=0.75*THb$; however, there may be situations in which this assumption is not valid.

The following flows from the definition of x:

$$(1-x)THb*SaO_2=HBO_{2A}$$

Substituting the above in the expression for $SvO_2$ and reducing the expression yields:

$$SvO_2=SaO_2+(1/x)(StO_2-SaO_2).$$

ALTERNATIVES

In general the disclosed technique may utilize optical sources other than lasers, such as light emitting diodes (LEDs) for example.

As mentioned, probes may be used in which the light sources and detectors are directly in contact with the skin, without using fibers to guide the light to/from the sample location.

Instead of performing frequency stepping sequentially, in alternative embodiments a comb generator may be used to generate modulation signals and modulate the sources at many modulation frequencies simultaneously.

The portability of the system can be further improved by implementing miniaturized fiber-coupled laser diodes and miniaturized current driver modules that can be housed in a portable device enclosure. This will help to more easily measure patients in a clinical setting for a range of applications, such as chemotherapy monitoring or rapid hemodynamic analysis. The speed of the system also opens the possibility of monitoring rapid physiological changes, specifically absolute concentrations of oxy- and deoxyhemoglobin at the cardiac rate, which may be useful in monitoring hemodynamics related to conditions such as peripheral artery disease.

While various embodiments of the invention have been particularly shown and described, it will be understood by those skilled in the art that various changes in form and details may be made therein without departing from the scope of the invention as defined by the appended claims.

What is claimed is:

1. A tissue oximetry system, comprising:
    an optical subsystem including a plurality of optical sources and one or more optical detectors, the optical sources being configured and operative to generate a set of optical signals of distinct wavelengths modulated according to respective RF modulation signals applied thereto, the set of wavelengths and the RF modulation signals selected according to a model for (1) obtaining absorption values and scattering values from per-wavelength amplitude and phase responses, and (2) obtaining measurements of blood oxygen values from the absorption and scattering values for the wavelengths, the optical signals collectively forming an incident optical signal configured to be directed to a sample location of a tissue, the one or more optical detectors being configured and operative to generate one or more analog detection signals indicative of amplitude and phase of RF modulation components of a detected optical signal emanating from the sample location in response to the incident optical signal; and
    an electronics and processing subsystem including a set of signal sources, an analog-to-digital conversion circuit, data acquisition circuitry, and a processor, the signal sources being configured and operative to generate respective ones of the RF modulation signals based on corresponding RF modulation command values from the processor, the analog-to-digital conversion circuit being configured and operative to generate respective streams of raw digital sample values from the analog detection signals, the data acquisition circuitry and processor being co-configured and co-operative to:
        (1) provide the RF modulation command values to the signal sources in synchronism with sampling operation of the analog-to-digital conversion circuit and according to an offset pattern and rate that includes stepping through an RF range for each of the RF modulation signals according to the model, using a predetermined step size, the stepping being performed at a sufficiently high rate to obtain measurements of the absorption value and the scattering value for each of the wavelengths in each of respective measurement intervals at least 10 times per second, and
        (2) in each of the measurement intervals, calculate the model to obtain one or more respective blood oxygen values from the respective measurements of the absorption values and scattering values of the measurement interval, and display or otherwise use the obtained blood oxygen values in higher-level diagnostic assessment of the blood oxygenation of the tissue.

2. The tissue oximetry system of claim 1, wherein the model relates a set of absorption-versus-wavelength characteristics for the wavelengths and respective values of the blood oxygen values as chromophores.

3. The tissue oximetry system of claim 2, wherein the blood oxygen values as chromophores include oxyhemoglobin and deoxyhemoglobin.

4. The tissue oximetry system of claim 1, wherein the model is a diffusion model relating a measured amplitude attenuation function and measured phase lag function to the absorption and scattering values, the amplitude attenuation function and phase lag functions being functions of frequency in the RF range for each of the wavelengths.

5. The tissue oximetry system of claim 1, wherein the blood oxygen values include oxyhemoglobin and deoxyhemoglobin, and the processor is further configured and operative to calculate derived values including total hemoglobin, total oxygen saturation, arterial oxygen saturation, and venous oxygen saturation.

6. The tissue oximetry system of claim 1, wherein the signal sources include direct digital synthesizers generating the RF modulation signals by digital synthesis and digital-to-analog conversion based on the corresponding RF modulation command values.

7. The tissue oximetry system of claim 1, wherein the optical subsystem includes an optical combiner combining the optical signals into the incident optical signal configured to be directed to the sample location of tissue.

8. A method of operating a tissue oximetry system to obtain blood oxygen values for a tissue, comprising:
    directing an incident optical signal to a sample location of the tissue, the incident optical signal formed by a set of optical signals of distinct wavelengths modulated according to respective RF modulation signals applied thereto, the set of wavelengths and the RF modulation signals selected according to a model for (1) obtaining absorption values and scattering values from per-wavelength amplitude and phase responses, and (2) obtaining measurements of the blood oxygen values from the absorption and scattering values for the wavelengths;
    generating one or more analog detection signals from a detected analog optical signal emanating from the sample location in response to the incident optical signal, the analog detection signals indicative of amplitude and phase of RF modulation components of the detected optical signal; and
    generating the RF modulation signals in synchronism with sampling operation of analog-to-digital conversion circuitry and according to an offset pattern and rate that includes stepping through an RF range for each of the RF modulation signals according to the model, using a predetermined step size, the stepping being performed at a sufficiently high rate to obtain measurements of the absorption value and the scattering value for each of the wavelengths in each of respective measurement intervals at least 10 times per second, and
    in each of the measurement intervals, calculate the model to obtain the blood oxygen values from the respective measurements of the absorption values and scattering values of the measurement interval, and display or otherwise use the obtained blood oxygen values in higher-level diagnostic assessment of the blood oxygenation of the tissue.

9. The method of claim 8, wherein the model includes a first model relating a set of absorption-versus-wavelength characteristics for the wavelengths and respective values of the blood oxygen values as chromophores.

10. The method of claim 9, wherein the blood oxygen values as chromophores include oxyhemoglobin and deoxyhemoglobin.

11. The method of claim 8, wherein the model includes a second model being a diffusion model relating a measured amplitude attenuation function and measured phase lag function to the absorption and scattering values, the amplitude attenuation function and phase lag functions being functions of frequency in the RF range for each of the wavelengths.

12. The method of claim 8, wherein the blood oxygen values include oxyhemoglobin and deoxyhemoglobin, and further including calculating derived values including total hemoglobin, total oxygen saturation, arterial oxygen saturation, and venous oxygen saturation.

13. The method of claim 8, further including generating the RF modulation signals by digital synthesis and digital-to-analog conversion based on the corresponding RF modulation command values.

14. The method of claim 8, further including combining the optical signals into the incident optical signal configured to be directed to the sample location of tissue.

\* \* \* \* \*